United States Patent
Alt et al.

(10) Patent No.: US 9,775,532 B2
(45) Date of Patent: Oct. 3, 2017

(54) REMOTE CONTROL OF IMPLANTABLE DEVICE THROUGH MEDICAL IMPLANT COMMUNICATION SERVICE BAND

(75) Inventors: Eckhard Alt, Munich (DE); John Philip Brinkmann, Houston, TX (US)

(73) Assignee: Medtronic, Inc., Minneapolis, MN (US)

( * ) Notice: Subject to any disclaimer, the term of this patent is extended or adjusted under 35 U.S.C. 154(b) by 1311 days.

(21) Appl. No.: 11/852,746

(22) Filed: Sep. 10, 2007

(65) Prior Publication Data

US 2007/0299349 A1    Dec. 27, 2007

Related U.S. Application Data

(63) Continuation of application No. 11/077,046, filed on Dec. 7, 2004, now abandoned, which is a
(Continued)

(30) Foreign Application Priority Data

Oct. 1, 2001 (DE) .................................. 101 48 440

(51) Int. Cl.
*A61B 5/05* (2006.01)
*A61B 5/04* (2006.01)
(Continued)

(52) U.S. Cl.
CPC ........ *A61B 5/04012* (2013.01); *A61B 5/0031* (2013.01); *A61B 5/0205* (2013.01);
(Continued)

(58) Field of Classification Search
CPC .............. A61N 1/3627; A61N 1/36521; A61B 5/04012; A61B 5/0031; A61B 5/0537;
(Continued)

(56) References Cited

U.S. PATENT DOCUMENTS 4,884,576 A    12/1989  Alt
4,899,758 A    2/1990   Finkelstein et al.
(Continued)

OTHER PUBLICATIONS

Louis, et al., "A systematic review of telemonitoring for the management of heart failure," The European journal of Heart Failure 5 (2003) 583-590.
(Continued)

*Primary Examiner* — Rex R Holmes (57) ABSTRACT

A system and method for communicating data and signals through the Medical Implant Communication Service Band using a repeater or base station in the proximity to an implantable device within a patient is disclosed. In a preferred embodiment, the device is capable for early detection and monitoring of congestive heart failure in a patient. Impedance measurements, or other health parameters depending on the type of implantable device or sensor used, are sent using a bi-directional low-power radio operating in the MICS band to a nearby base station which may provide signal processing and analysis. The base station may have an interface to one or more communications networks to connect to a remote location. The system and method of the present invention permits a healthcare professional to monitor an ambulatory patient's condition at a remote location and to program the implanted device.

1 Claim, 8 Drawing Sheets

Related U.S. Application Data continuation-in-part of application No. 10/622,184, filed on Jul. 16, 2003, now Pat. No. 8,777,851, which is a continuation-in-part of application No. 10/155,771, filed on May 25, 2002, now Pat. No. 6,829,503.

(51) Int. Cl.
*A61B 5/00* (2006.01)
*A61B 5/0205* (2006.01)
*A61B 5/053* (2006.01)
*A61N 1/362* (2006.01)
*A61B 5/08* (2006.01)
*A61N 1/365* (2006.01)

(52) U.S. Cl.
CPC .......... *A61B 5/0537* (2013.01); *A61N 1/3627* (2013.01); *A61B 5/0809* (2013.01); *A61B 5/7232* (2013.01); *A61B 2560/0271* (2013.01); *A61B 2562/0219* (2013.01); *A61N 1/36521* (2013.01)

(58) Field of Classification Search
CPC ................ A61B 5/0205; A61B 5/7232; A61B 2562/0219; A61B 2560/0271; A61B 5/0809
USPC ......................................... 607/30–32, 57, 60
See application file for complete search history.

(56) References Cited

U.S. PATENT DOCUMENTS

| | | | |
|---|---|---|---|
| 5,331,966 A | 7/1994 | Bennett et al. | |
| 5,876,353 A | 3/1999 | Riff | |
| 5,899,928 A | 5/1999 | Sholder et al. | |
| 5,920,310 A | 7/1999 | Faggin et al. | |
| 5,957,861 A * | 9/1999 | Combs et al. | 600/547 |
| 5,987,352 A | 11/1999 | Klein et al. | |
| 6,080,187 A * | 6/2000 | Alt et al. | 607/32 |
| 6,104,949 A | 8/2000 | Pitts Crick et al. | |
| 6,141,588 A * | 10/2000 | Cox et al. | 607/9 |
| 6,190,324 B1 | 2/2001 | Kieval et al. | |
| 6,336,903 B1 | 1/2002 | Bardy | |
| 6,351,667 B1 | 2/2002 | Godie | |
| 6,416,471 B1 | 7/2002 | Kumar et al. | |
| 6,497,655 B1 | 12/2002 | Linberg et al. | |
| 6,512,949 B1 | 1/2003 | Combs et al. | |
| 6,600,949 B1 | 7/2003 | Turcott | |
| 6,752,765 B1 * | 6/2004 | Jensen et al. | 600/536 |
| 6,829,503 B2 | 12/2004 | Alt | |
| 2002/0115939 A1 | 8/2002 | Mulligan et al. | |
| 2003/0114898 A1 | 6/2003 | Von Arx | |
| 2003/0139783 A1* | 7/2003 | Kilgore et al. | 607/49 |

OTHER PUBLICATIONS

Valina, et al., "Subcutaneous Impedance Monitoring for Detection of Low Cardiac Output and Fluid Overload," American Heart Association Scientific Sessions 2003, abstract tracking No. 03-SS-A-17350-AHA.

Langreth, "The Doctor Is In: predicting and treating disease will get a whole lot easier when monitors are implanted," Forbes Magazine article dated Sep. 15, 2003.

47 C.F.R. § 95.628.

* cited by examiner

REMOTE CONTROL OF IMPLANTABLE DEVICE THROUGH MEDICAL IMPLANT COMMUNICATION SERVICE BAND

CROSS-REFERENCE TO RELATED APPLICATIONS

This application is a continuation of U.S. patent application Ser. No. 11/007,046, filed Dec. 7, 2004, now abandoned, which is a continuation-in-part of U.S. patent application Ser. No. 10/622,184, filed Jul. 16, 2003 now U.S. Pat. No. 8,777,851, which is a continuation-in-part of U.S. patent application Ser. No. 10/155,771, filed May 25, 2002, now U.S. Pat. No. 6,829,503, issued Dec. 7, 2004, claiming priority of the German Patent Serial No. 101 48 440.2, filed Oct. 1, 2001. These applications are hereby incorporated by reference in their entireties, and priority is claimed to them.

BACKGROUND OF THE INVENTION

This invention relates to electronic medical devices that are implanted in the body of a patient. More particularly, it relates to a congestive heart failure monitor for detecting and monitoring the progression of congestive heart failure and the method of remote control and communication with the device.

Many patients who have suffered one or more myocardial infarctions subsequently require treatment for congestive heart failure (CHF). The left heart fails while the pumping function of the right heart remains adequate, because the latter has only about 20% of the workload of the former. This leads to an increase in blood volume congested to the lungs, resulting in pulmonary congestion, build up of increased levels of fluid, and congestion of internal organs including the stomach and intestines. Increased fluid in the stomach and intestines reduce their ability to absorb drugs prescribed for treatment of CHF, particularly diuretics. The congestion is often accompanied by a worsening of myocardial function, with consequent drop in blood pressure and reduced renal perfusion, which only further aggravates the congestive situation. Thus, late recognition of congestion leads to increased dosages of oral diuretics that are unsuccessful to treat the condition, ultimately requiring that the patient be hospitalized.

Avoidance of hospitalization and the pitfalls of late treatment require detection of CHF at an early stage, so that the prescribed drugs can be fully absorbed and effective. If detected early, a combination of diuretics and other drugs can slow the progress of the disease and allow the patient to enjoy an improved lifestyle.

An extensive review of telemonitoring for the management of heart failure by Louis et al. has been published in the past in the European Journal of Heart Failure. The conclusion of this article is that telemonitoring might have an important role as a strategy for delivery of effective health care for patients with heart failure. However, the current state of the art still lacks an adequate means to monitor the data and to communicate data.

The ApexPro FH enhances patient safety by using a bi-directional, frequency-hopping infrastructure to help ensure that patient data is transmitted clearly and completely to a central patient monitoring station. While this system is based on external data and provided by GE Healthcare using a Unity Network, the use of the medical implant communication service band is not part of the system nor is an implantable device considered to be part of the communication system. This system relies rather on data external to the patient.

Several patents have looked into impedance monitoring and data processing and monitoring and diagnosing hypertension or congestive heart failure in patients. Among those is Riff, U.S. Pat. No. 5,876,353 which describes an Impedance Monitor for Discerning Edema through Evaluation of Respiratory Rate. U.S. Pat. No. 5,957,861, Combs et al. and its continuation, U.S. Pat. No. 6,512,949 describes an Implantable Medical Device for Measuring Time Varying Physiologic Conditions Especially Edema and for Responding Thereto. The U.S. Pat. No. 6,104,949, Pitts Crick et al. relates to a device and method used for the diagnosis and treatment of congestive heart failure. Specifically, this invention senses a trans-thoracic impedance as well as patient posture and correlates changes in posture with trans-thoracic impedance in order to assess the degree of congestive heart failure. The Device for Detecting Pericardial Effusion, Godie et al., U.S. Pat. No. 6,351,667 describes an apparatus for detecting pericardial effusion that includes a measurement apparatus connected to a wire probe to be anchored to the right heart ventricle and two other wire probes to measure the impedance between different probes in order to assess the degree of pericardial effusion. U.S. Pat. No. 4,899,758, Finkelstein et al., describes a Method and Apparatus for Monitoring and Diagnosing Hypertension and Congestive Heart Failure, by using C2 and brachial artery pulses to discriminate a threshold of certain Windkessel function. U.S. Pat. No. 6,336,903, Bardy et al. relates to an automatic system and method for diagnosing and monitoring congestive heart failure and outcomes thereof. A plurality of monitoring sets are retrieved from a database and each patient's status change is tested against an indicator threshold corresponding to the same type of patient information as the recorded measures to which it was compared. The indicated threshold corresponds to a quantifiable physiological measure of a pathophysiology indicative of congestive heart failure. U.S. Pat. No. 6,416,471, Kumar et al., describes a Portable Remote Patient Telemonitoring System. This invention has useful application to the connection of patient data during drug trials and medical testing for regulatory approvals as well as the management of patients with chronic disease. U.S. Patent Publication No. 2002/0115939, Mulligan et al. describes an Implantable Medical Device for Monitoring Congestive Heart Failure in which incremental changes in a parameter data over time provide insight into the heart failure state of the patient's heart.

None of those previous disclosures however describes adequate means to communicate those signals in a safe way between an implant device and an external data handling and coordinating center.

It is a principal aim of the present invention to provide an implantable heart failure monitor which is capable of achieving very early detection of CHF. It is a further aim of the present invention to describe the method of remote controlling an implanted diagnostic or therapeutic electronic device in uni- or bi-directional ways.

SUMMARY OF THE INVENTION

The implantable medical device of the present invention may be of size smaller than a typical pacemaker device—about the size of a thumb. It may be implanted in a subcutaneous pocket formed by a surgeon in the patient's chest, under local anesthesia and minimally invasive requirements. The device includes a hermetically sealed can with appropriate electronic circuitry inside. A set of device-mounted electrodes may be used to measure the impedance of the adjacent tissue and most especially the lung tissue. The progressive retention of fluid in the lungs and congestion of the ventricle together result in a reduced resistance measurement that is monitored either continuously or periodically by the device.

In a preferred mode of operation, the device alerts the patient and/or the attending physician when a diagnostic threshold is reached which is indicative of the progression of CHF. The overall architecture of the device follows implantable practice, however, it should be appreciated that the partitioning of the device is flexible and the division of sensing and analysis structures can be shared between implanted and external (remote, i.e., non-implanted) devices. A low-power radio transceiver operating in the Medical Implant Communications Service (MICS) band can be use for linking the device to a proximate base station. The base station can communicate with one or more remote locations via telecommunications or wideband networks to permit monitoring patient data and programming the device remotely.

The Medical Implant Communications Service is an ultra-low power, unlicensed, mobile radio service for transmitting data in support of diagnostic or therapeutic functions associated with implanted medical devices. The MICS permits individuals and medical practitioners to utilize ultra-low power medical implant devices, such as CHF monitors, cardiac pacemakers and defibrillators, without causing interference to other users of the electromagnetic radio spectrum. No licensing is required, but MICS equipment is intended for operation only by healthcare professionals.

Signal processing may be performed entirely internally within the device, or the device may operate as a data logger and communicate with an external base station which participates in data reduction and analysis.

Although specific structures are shown as being dedicated to specific tasks, it should be apparent that certain functions may be shared if the device is integrated with other diagnostic or therapeutic devices. For example, the electrode set used to determine the impedance of the lungs could be used for additional purposes.

It is an object of the present invention to provide a device-implemented method of detecting and monitoring congestive heart failure in a patient wherein the body portion encompasses the patient's heart, including performing impedance measurements by means of a signal injected into the body portion from the device and retrieved as a signal subdivided into a cardiac portion, a pulmonary portion, and a total impedance portion.

It is a further object of the present invention to provide a method of remote control of an implantable device through the Medical Implant Communication Service band by changing the settings, function, characteristics or parameters of the implantable device via bi-directional communication through the MICS band of 402 to 405 MHz.

It is a further object of the present invention to provide a method of remote control using a local repeater base station that communicates bi-directionally and transmits signal to the implant device on one end and communicates and transmits the signal through a telephone land line, wireless telephone, or through a network such as the Internet to a control station on the other end.

It is a further object of the present invention to provide a patient monitoring system with an implantable device wherein the implantable device is one of a congestive heart failure monitoring device, a cardiac pacemaker, defibrillator, neurostimulator, muscle stimulator, gastric stimulator, or diagnostic implantable device for monitoring a variety of physiologic body functions such as $CO_2$, blood pressure, oxygen, glucose, ventilation, heart rate, activity, posture, hormones, cytokines, or neurofunctions.

It is a further object of the present invention to provide a system for remote control of an implantable device through the Medical Implant Communication Service band capable of changing the settings, functions, characteristics or parameters of an implantable device via bi-directional communication through the MICS band of 402 to 405 MHz.

It is a further object of the present invention to provide a method of communicating data with an implantable device through Medical Implant Communication Service band using a repeater in proximity to the patient.

It is a further object of the present invention to provide a method of communicating data using a local repeater in proximity to a patient capable of communicating bi-directionally that communicates with the implantable device on one end and translates or amplifies the signals with a data handling and coordinating center on the other hand through an Internet or wireless Internet connection.

It is a further object of the present invention to provide a method of communicating patient-derived data originating from an implantable device between a data handling and coordinating center and a local patient care physician center.

BRIEF DESCRIPTION OF THE DRAWINGS

The above and other aims, objectives, aspects, features and attendant advantages of the invention will be further understood from a reading of the following detailed description of the best mode presently contemplated for practicing the invention, taken with reference to certain presently preferred implementations and methods, and in conjunction with the accompanying drawings, in which.

DETAILED DESCRIPTION

The device of the preferred embodiment of the invention is disclosed in the preferred implementation as being a stand-alone diagnostic device to simplify the description of its operation. Throughout the several views of the drawings identical reference numerals indicate identical structure. Views of the device either alone or as implanted are not intended to represent actual or relative sizes.

Figure 1:
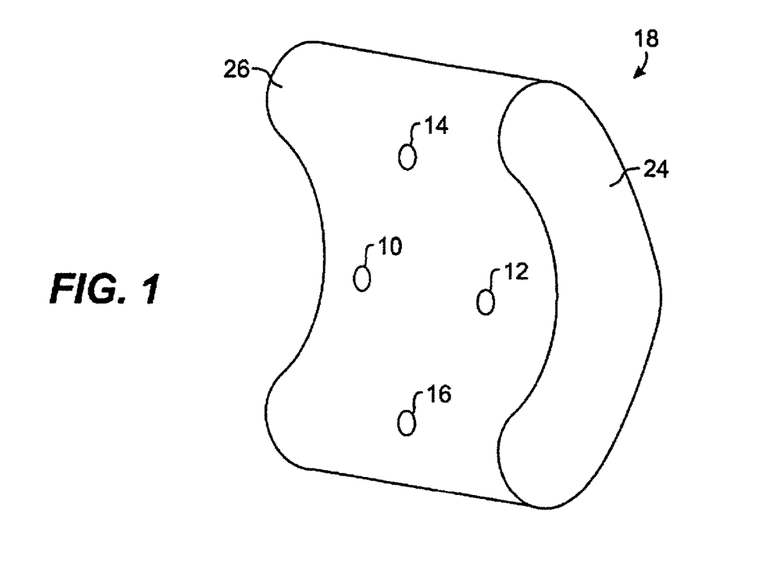
FIG. 1 is an exterior view of an embodiment of the device.

FIG. 1 illustrates the exterior of the device 18 in its presently preferred embodiment. Device 18 includes a circuit module (to be discussed below in conjunction with the description of FIG. 3) within a hermetically sealed "can" or case 24 composed, for example, of titanium. The size of the case 24 is clearly dictated by the size of the internal circuit components and wiring included printed circuit board(s) and other forms, but preferably is very small, currently about 5.0 cm long by 2.0 cm wide by less than 1.0 cm thick.

Case 24 is a standard rectangular case with rounded edges and a header of epoxy resin on top (not shown in FIG. 1). In one preferred embodiment, Case 24 has a curvilinear shape which presents a concave shape or surface 26 on one side (in contrast to an edge of the case) and a convex shape on the opposite side of the case. Four surface mounted electrodes 10, 12, 14 and 16 are positioned in spaced-apart relationship on the slightly concave surface 26, with each electrode being electrically insulated from the case 24 itself. The electrodes should be of low polarization, preferably composed of or coated with iridium oxide. By way of example, "inner" electrodes 10 and 12 are spaced apart on the concave side inward of opposite edges and centrally along the length of the case, while "outer" electrodes 14 and 16 are spaced farther apart—preferably, by at least about 4 cm—on that same side inward of opposite edges and centrally along the width of the case. The shape of the case is designed (and preferred) to conform to the shape of the anatomy of the human chest. With the concave side of the case placed toward the interior of the body within the implant site of device 18, the device is prevented from turning within its subcutaneous pocket which would otherwise position the surface electrodes at the wrong side—namely, toward the exterior of the patient's body. The reason for this positioning will become apparent as the description proceeds.

Figure 2:
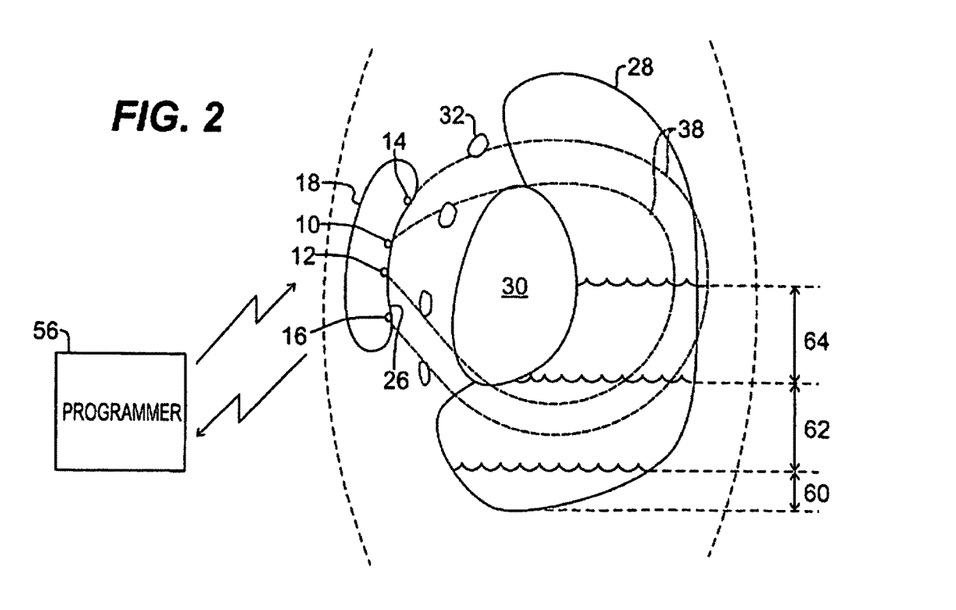
FIG. 2 is a schematic representation of an implantation of the device in the body of a patient.

The most preferred implant site of the device is the left lower anterior lateral hemithorax of the patient's body as shown in FIG. 2. In part, this is because optimal sensing occurs with the device placed slightly to the left of the patient's midline. FIG. 2 illustrates in schematic form a side view of a patient (in phantom) with the device 18 implanted in a pectoral of the chest over the basal region of lungs 28 and heart 30, outside the rib cage 32. An implantation at the preferred site places the device on the left anterior thorax side between the 5th and 6th intercostals space. In this position of the device, an impedance signal is developed which represents the impedance of the lungs and heart tissue by virtue of current injected into the circuit path that establishes a field through that portion of the body from device 18.

Figure 3:
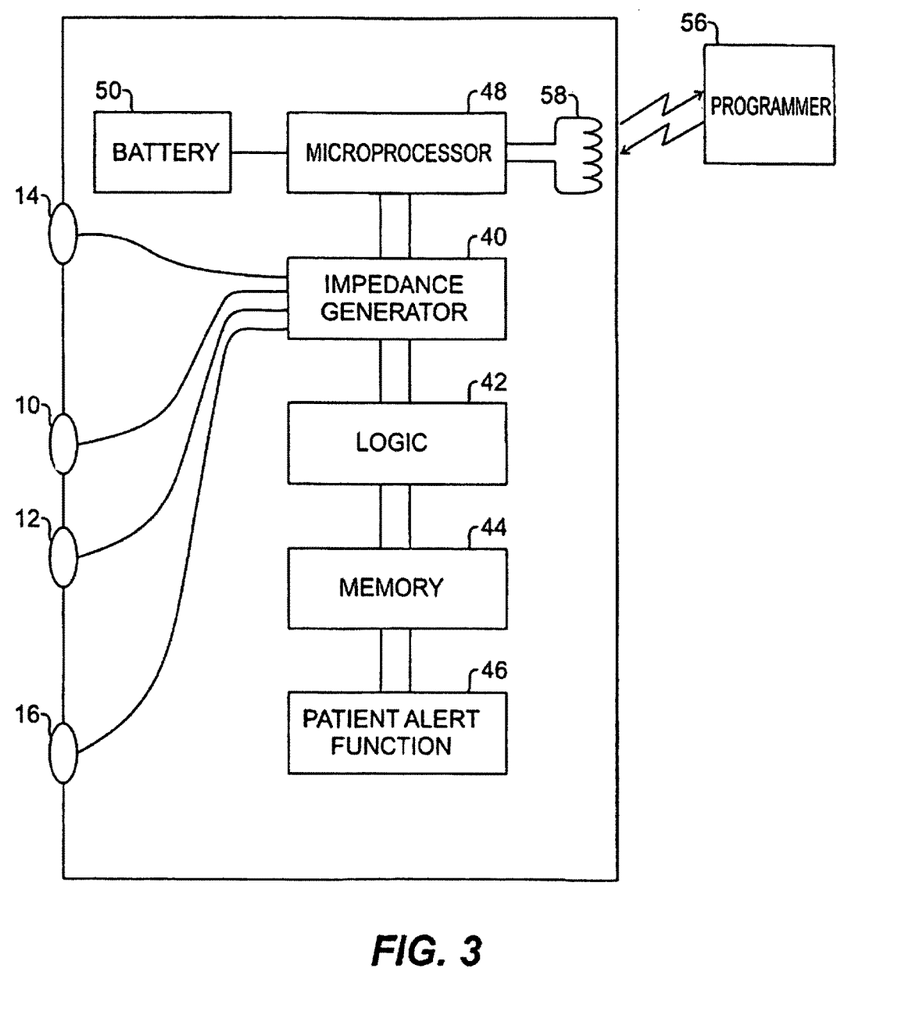
FIG. 3 is a block diagram of the internal circuitry of the device.

FIG. 3 illustrates the exemplary circuit module within device 18. An impedance signal generator 40 injects signal current into the body, preferably through "inner" electrodes 10 and 12. The current traverses the circuit path through the body portion of interest and has a return path through "outer" electrodes 14 and 16. Field lines 38 (FIG. 2) attributable to current flowing from the electrodes emanate from the concave side 26 of device 18, and, together with the electrode spacing, define the "viewing volume" of the device for the impedance sensing circuitry. Electrode spacing of at least four cm between the outer electrodes 14, 16 will allow a measurement to a depth of up to 10 cm of lung tissue in the anterior lateral lower left thorax. The field lines produced by current through the circuit path intersect the lung tissue 28 and are somewhat less influenced by the volume of the heart 30.

The circuit module within device 18 is powered by a preferably lithium-ion battery 50. Impedance generator 40 is controlled by microprocessor 48, as is logic 42 for analysis and memory 44 for data. Measured values of impedance are stored in memory 44, and used by microprocessor 48 to calculate various functions of the measured impedance values. A threshold detector 46 may be incorporated in device 18 as a patient alert function or alarm (e.g., by emitting an acoustic signal, vibrations, or low level pulses for local muscle contractions, recognizable by the patient) indicative of a need for immediate intervention when impedance associated with fluid level 64, for example, is detected. Such an alarm condition may also be signaled by telemetry from an antenna or coil 58 within the circuit module at the microprocessor, normally used to transmit the other impedance data, to a remote programmer 56 to monitor and log the progress of the disease and the therapeutic effect of treatment for review by the patient's physician.

In a preferred embodiment, the device is adapted to monitor impedance at a digital rate of 128 Hz, for partitioned analysis of contractile cardiac function, pulmonary ventilation function and long term pulmonary impedance, over an average of 72 hours or more. Signal processing allows deviation from basic impedance of the body region of interest, especially the lungs, to be detected as an early monitoring of a decrease in lung impedance, indicative of increasing congestion by fluid content in the lungs. The decrease in lung impedance associated with CHF occurs as the lungs fill with fluid, which is a considerably better electrical conductor than the normal lung tissue. Exemplary values of impedance for lung tissue are 400-1,000 ohms per centimeter ($\Omega$/cm), compared with 50 $\Omega$/cm for fluid.

Representative fluid levels accumulated in the lungs are illustrated in FIG. 2 at 60, 62 and 64. Level 60 represents the relative additional amount of fluid associated with normal lung function. Level 62 represents the relative amount of fluid present for a compromised lung function associated with CHF. And level 64 is the relative still additional amount of fluid associated with severely reduced lung function requiring immediate attention, indicative of advanced CHF.

The device 18 may be designed to provide a threshold or trigger level at an accumulation of fluid corresponding approximately to level 64. Algorithms are used to convert real time measurements into a diagnostic indication of congestion. The device may be operated continuously and the impedance data are then analyzed in kind. ECG data may be used additionally, detected at the outer electrodes 14 and 16 to improve the capability of the device to discern impedance changes in the heart.

Figure 4:
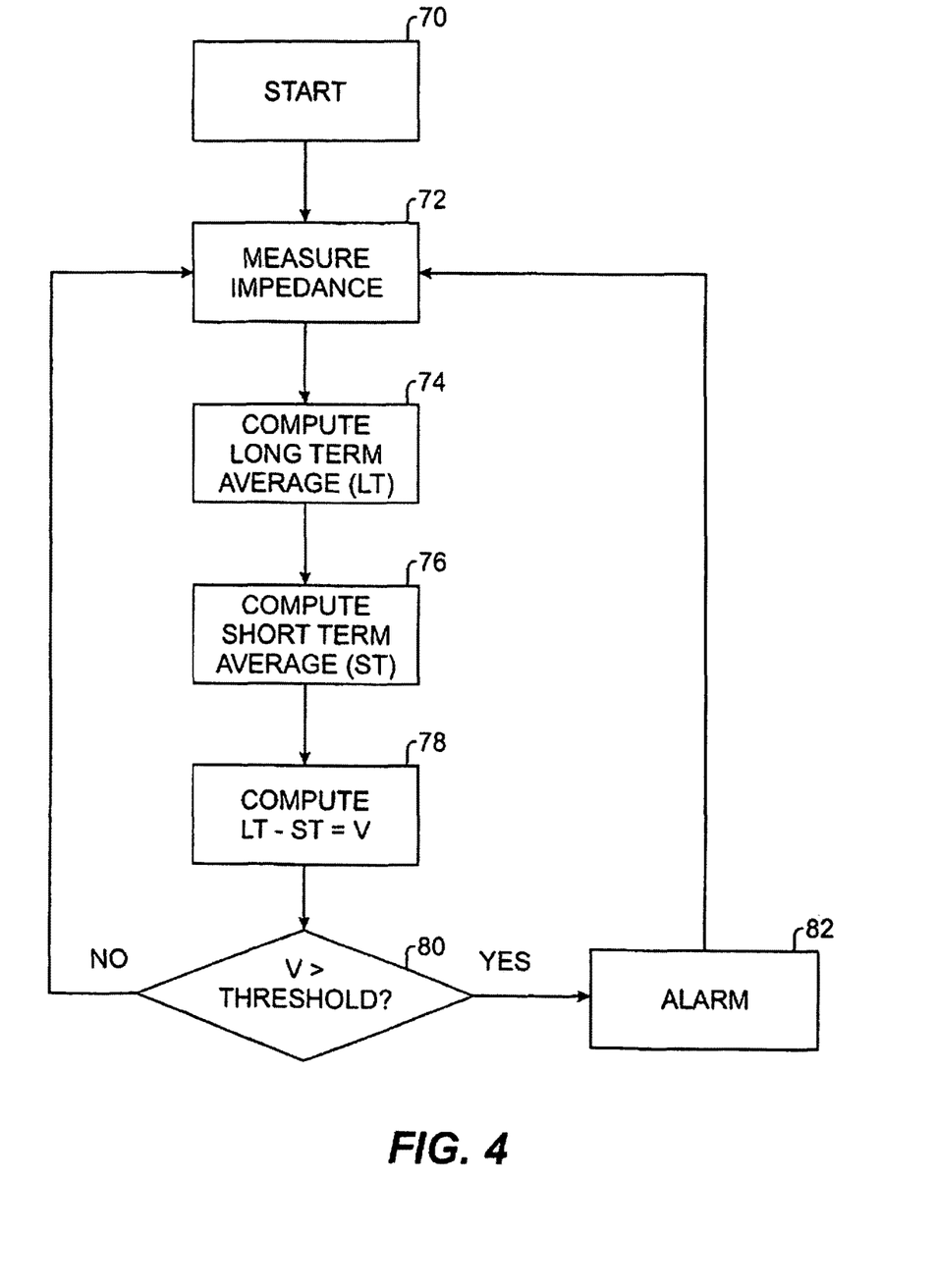
FIG. 4 is a flow chart illustrating the operation of the device.

FIG. 4 is a flow chart of an exemplary detection algorithm used by the device 18. On commencement, counters are initialized and impedance generator 40 is turned on to inject signal current into the body via the inner pair of electrodes 10, 12 (start, 70). The impedance signal current is preferably a rectangular biphasic pulse wave at a rate of 128 Hz and a peak-to-peak amplitude of 1 milliampere (ma), or, alternatively, an alternating current in a range from 5 microamperes (μa) to 10 μa. The pulses may be injected with considerably higher energy content than the AC wave because of their very short duration (e.g., 15 μsec or less), with no risk of myocardial depolarization, and are capable of detecting cardiac changes as well as pulmonary changes.

Impedance is then calculated (72) from a measurement of the resulting voltage at the outer pair of electrodes 14, 16. Alternatively, a fixed voltage may be applied across the excitation (inner) electrodes and the resulting current measured at the measurement (outer) electrodes reflects the impedance. A long-term average of the impedance value is computed (74), covering a period ranging from days to weeks as a running average. A short-term average of the impedance value is also computed (76), covering a period from hours to days. The difference between the long-term (LT) and short-term (ST) averages is calculated (78) as a slope measurement (V) indicative of deterioration of the lung condition, to detect accelerating lung congestion. If the value V exceeds a predetermined threshold (slope) value (80), an alarm condition is indicated and the patient alert function (46, FIG. 3) is initiated. In either case (an alarm condition or not), another impedance measurement is performed (72) and the processing cycle is repeated.

In the description of FIG. 2, the detection of lung congestion requiring immediate attention was the result of a simple volume measurement. In practice, however, a slope measurement is preferred to determine when an alarm condition is occurring or has occurred, because the variability of impedance signals makes it more difficult to achieve accurate threshold detection by volume measurement.

Figure 5:
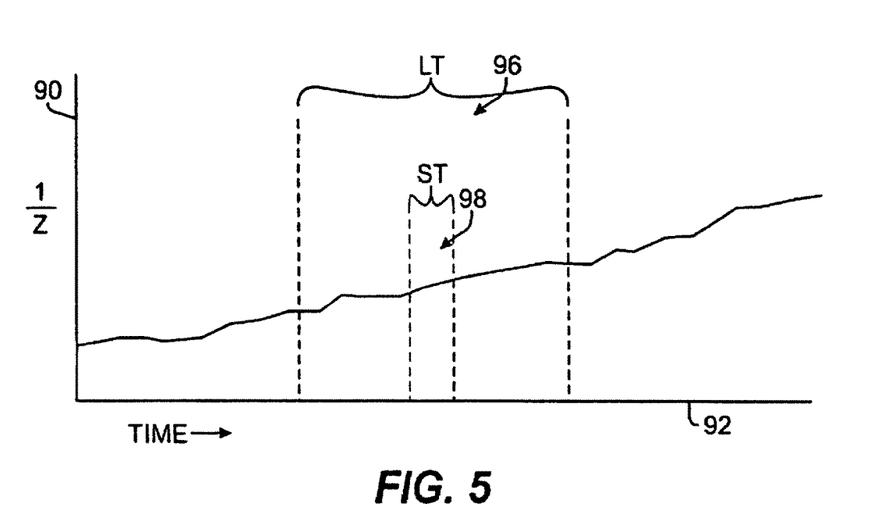
FIG. 5 is a graph of the device operation in terms of the reciprocal of impedance versus time.

FIG. 5 is a graph of the device operation using the exemplary detection algorithm represented by the flow chart of FIG. 4. The vertical axis 90 is conductance, the reciprocal of impedance (1/Z). Therefore, the greater the lung congestion (i.e., the larger the fluid volume in the patient's lungs), the lower the value of the term 1/Z. The horizontal axis 92 represents time. The long-term average of the impedance measurement has a characteristic value that filters out the short-term variations of the measurement. In the Figure, the LT value 96 of curve or slope 94 exhibits a more gradual slope than the ST value 98. The difference between the two is used to determine whether an alarm condition is occurring (LT−ST=V≥threshold).

In addition to the baseline impedance, impedance measurements at the frequency of 128 Hz can detect impedance changes with every pumping cycle, to provide indirect information on stroke volume, heart rate, and cardiac output calculated therefrom. Additionally, by adequate low pass filtering, the indirect tidal volume of ventilation can be separated out, as well as respiratory rate. Typically, ventilation is in a range from 0.2 Hz to 0.8 Hz, while cardiac events are in a range from 1 Hz to 3 Hz. Both subsignals, cardiac and ventilation, are used in addition to determine congestive heart failure indicated by increase in stroke volume, decrease in tidal volume, increase in heart rate, and increase in ventilation rate.

A power saving can be achieved in the device by limiting the impedance measurement to fixed periods separated by intervals of no measurement, or even sporadic measurements, rather than performing continuous impedance measurements.

The impedance measurement electrodes may be used to monitor the patient's ECG, as well as to obtain the raw data necessary for calculating absolute impedance and long- and short-term averages of impedance. Also, the cardiac- and ventilation-derived impedance phenomena may be correlated to the ECG for better evaluation. In addition, a miniaturized accelerometer within the case might give valuable information with regard to the daily and comparative physical activity of the patient.

It is important to consider the factor of where the measurements are taken as well as the manner of obtaining the measurements. For example, the spacing between the measurement electrodes 14, 16 determines the volume and area of measurement. By spacing these electrodes at least 4 cm apart, the depth of measurement is increased beyond only the tissue in the immediate vicinity of the electrode, to the tissue for which specific impedance and impedance changes are sought to be measured, typically to a depth of up to 10 cm of lung tissue. Also, performing the measurements on the patient's left side rather than the right side, and particularly on the anterior lateral lower left thorax, enables early detection of changes in left ventricular parameters and congestion in the lung circulatory system, rather than limiting the measurement to tissue and liver impedance which is primarily a function of congestion of the right heart. Additionally, at this preferred location for conducting the measurements, the cardiac phenomena and stroke volume dependent impedance changes are more easily detected than on the right side or the upper left thorax where impedance changes primarily follow blood circulation.

Due at least in part to the availability of advanced ultra low-power RF (radio frequency) capabilities, implanted devices such as the CHF monitor described above, pacemakers, defibrillators and medicine delivery pumps may communicate in real time or near real time with health professionals at a remote location. This communication can be facilitated by means of a repeater—a device for receiving electronic communication signals and delivering corresponding amplified ones. Even more desirable is a base station which may additionally process data received via such electronic communication signals prior to forwarding the data to a remote location.

Until recently, no globally accepted frequency band has been dedicated to medical implant device communications. Where communication between an implant and a monitoring system was required, most device manufacturers used short-range systems based on magnetic coupling between coils. These systems required extremely close coupling (less than 10 cm) between the medical device and programmer and offered limited data transfer rates.

This situation changed with the ITU-T Recommendation SA 1346, which outlined the shared use of the 402-405 MHz frequency band for a Medical Implant Communications Service (MICS). This recommendation has been implemented in the United States under the Federal Communications Commission (FCC) rules, and in Europe under the European Telecommunications Standards Institute (ETSI) Standard EN301 839. It is expected that MICS will become a true global standard within several years. Operations rules and technical regulations applicable to MICS transmitters may be found in 47 CFR 95.601-95.673 Subpart E.

The 402-405 MHz frequency band is available for MICS operations on a shared, secondary basis. The FCC determined that, compared to other available frequencies, the 402-405 MHz frequency band best meets the technical requirements of the MICS for a number of reasons. The 402-405 MHz frequencies have propagation characteristics conducive to the transmission of radio signals within the human body. In addition, equipment designed to operate in the 402-405 MHz band can fully satisfy the requirements of the MICS with respect to size, power, antenna performance, and receiver design. Further, the use of the 402-405 MHz band for the MICS is compatible with international frequency allocations. Finally, the U.S. Federal Communications Commission has determined that the use of the 402-405 MHz frequency band for the MICS does not pose a significant risk of interference to other radio operations in that band.

The 402- to 405-MHz band is well suited for in-body communications networks, due to signal propagation characteristics in the human body, compatibility with the incumbent users of the band (meteorological aids, such as weather balloons), and its international availability. The MICS standard allows 10 channels of 300 kHz each and limits the output power to 25 microwatts.

With rising healthcare costs, an aging population, and a growing acceptance of home-based medical monitoring, the MICS band is spurring advances in telemedicine. Using MICS, a healthcare provider can establish a high-speed, longer-range (typically 2 to 20 meters) wireless link between an implanted device and a base station. For example, an ultra low-power RF transceiver in a CHF monitor can wirelessly send patient health and device operating data to a bedside RF transceiver and vice versa. Data can then be forwarded from the base station via telephone land line, wireless cell phone communication, or the Internet to a doctor.

Advanced ultra low-power RF technology will dramatically improve the quality of life for patients with implanted medical devices. With a two-way RF link, doctors can remotely monitor the health of patients and wirelessly adjust the performance of the implanted device. This means fewer unnecessary hospital visits for the patient. Instead, with remote monitoring the doctor can call the patient in to the hospital when a problem is detected.

An implantable device such as a CHF monitor may be paired with a base station or repeater and linked by MICS transceivers. In such a system, data from the monitor may be downloaded to the base station for data processing and analysis using higher performance data processing equipment (which typically has higher power consumption than lower performance processors). Moreover, the base station may provide a communication interface to telecommunications networks such as the Public Switched Telephone Network (PSTN), computer networks including the Internet, and radio-based systems including cellular telephone networks, satellite phone systems and paging systems.

Such telecommunications can be used to send data to medical professionals who may use it to make treatment decisions including hospitalization, pharmaceutical dosage and/or measurement parameters of the implanted device. For example, if an increase in congestion is noted, more frequent measurements of impedance by the implanted device may be ordered by a physician via a return communications link.

Figure 6:
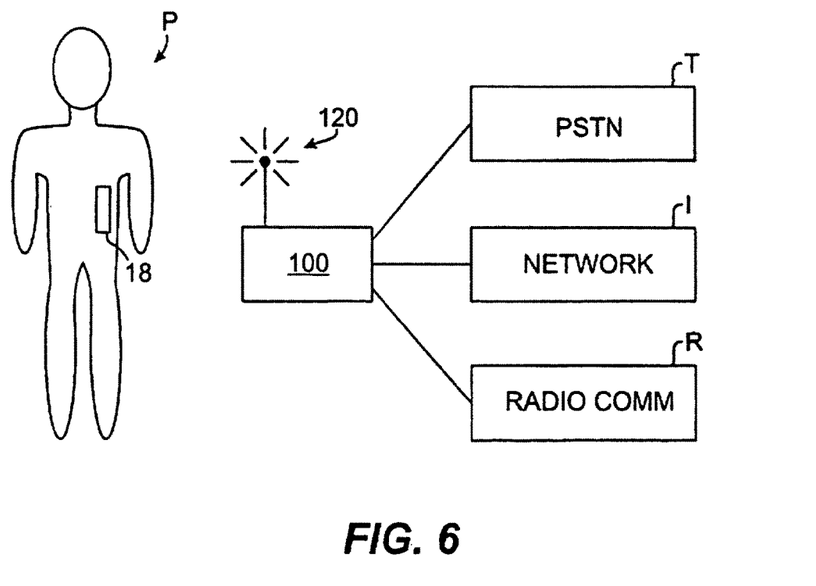
FIG. 6 is a schematic drawing of a system comprising an implanted device in a patient's body and a proximate base station having links to various telecommunication facilities.

A representative system is shown schematically in FIG. 6. A device 18 is implanted in patient P. Device 18 includes a short-range radio transceiver which utilizes the Medical Implant Communication Service. A corresponding transceiver in base station 100 receives data from device 18, processes and/or stores the data and sends it to a remote location using one or more of the Public Switched Telephone Network T, computer network I, and radio communications system R. Computer network I may be a local area network (LAN), wide area network (WAN), an intranet or the Internet. Radio communications system R may, in certain embodiments, be a cellular telephone system, the PCS system, a satellite phone system, a pager system or a two-way radio link.

In some embodiments, the link between the implanted device 18 and base station 100 may be a one-way link. For example, implanted device 18 may have a MICS transmitter (cf. transceiver) and base station 100 may have only a MICS receiver (cf. transceiver).

Figure 7A:
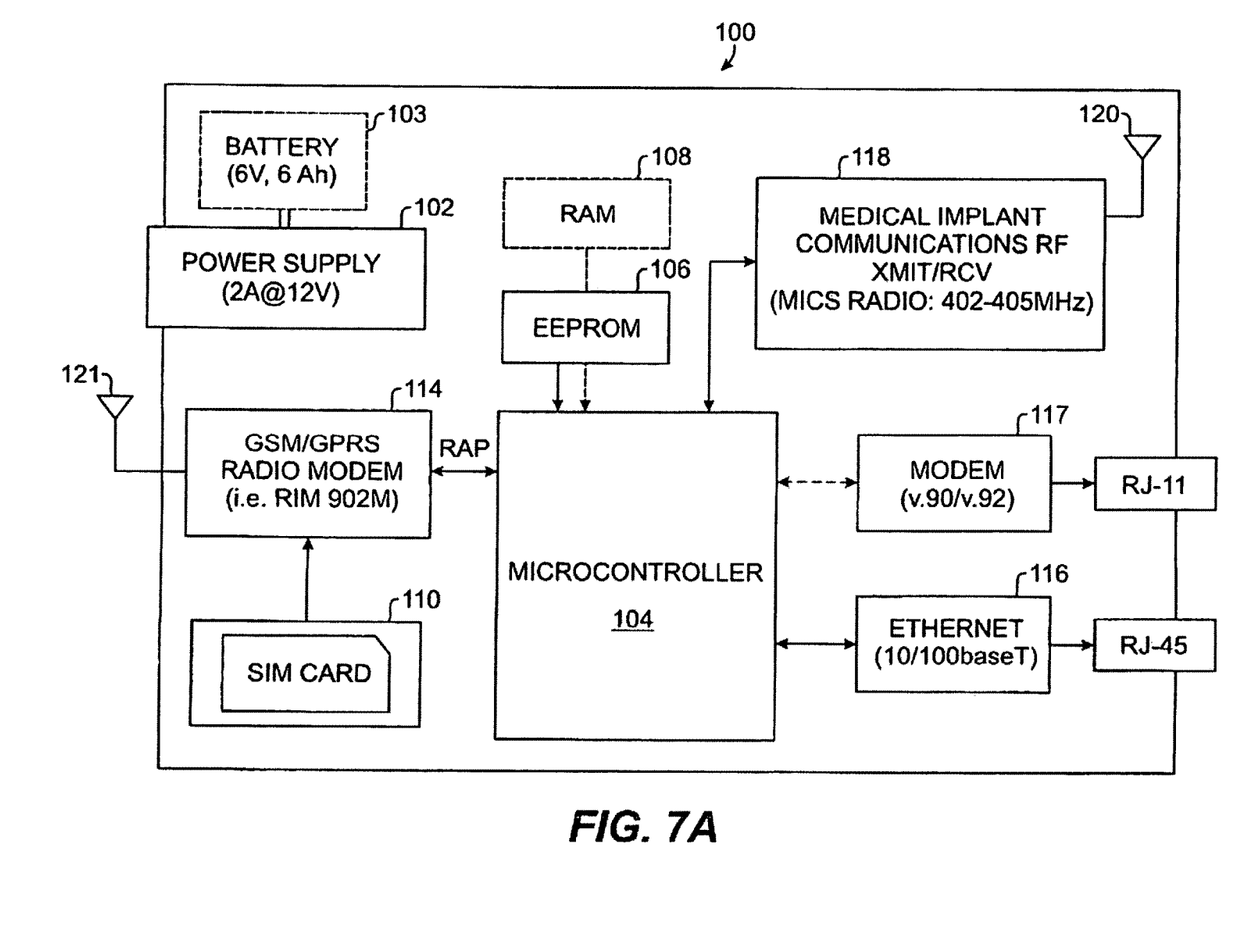
FIG. 7A is a block diagram of one embodiment of a base station according to the present invention.

FIG. 7A is a block diagram of an exemplary base station or repeater 100. A power supply 102 may rectify and covert ac line voltage to dc at the voltage level(s) required by the various subsystems within the base station. In some embodiments, power supply 102 may include an uninterruptible power supply (UPS) or battery 102 for operation during utility power interruptions or to permit brief operation of the base station at locations without external power. Power supply 102 may use an external wall transformer to deliver 9 or 12 volts DC to the system. An internal DC-DC converter may be used to step the voltage down to 3.3V (digital supply) and 5V (analog supply & radio(s) supply). An internal DC-DC converter may help to reduce noise (60 Hz line noise, etc). This would help the SNR (Signal to Noise Ratio) of both the wireless data radio modem, and the medical band radio—improving the range and efficiency of both.

Optional battery 103 can allow device operation for an extended period of time in the event of power interruption. A 6 Ah @ 6V battery could provide several days, if not a week of uninterrupted operation in the event of power failure. A lightweight battery can be used in a portable embodiment (for example, a 1000-1800 mAh lithium-ion battery could provide several days of portable operation)

Processor 104 may be a microprocessor or similar programmed system for implementing the methods of the system and controlling the various subsystems comprising base station 100. As noted above, one particularly significant advantage of base station 100 is its ability to use a powerful processor 104 whose electrical power consumption would be prohibitive for use within a battery-operated, energy sensitive implanted device such as CHF monitor 18. Microcontroller 104 may be a simple 8/16 bit microcontroller.

Attached EEPROM 106 may be used for code/firmware storage, or additionally used as a temporary storage location for cardiac data in the even that a network connection is not immediately available.

Attached RAM 108 may be used for code execution/scratchpad, or additionally used as a data buffer for cardiac data during transmit or receive.

Certain embodiments of base station 100 may include display or alarms (not shown) for displaying operational data and/or alerting the patient or caregiver of parameters which exceed defined limits.

For short-range communication with implanted device 18, base station or repeater 100 may include MICS transceiver 118 and antenna 120. Electrically small antennas are generally considered to be those with major dimensions less than 0.05 lambda, or in the MICS band, 37 mm. In some embodiments the corresponding antenna with which the base station or repeater 100 communicates may be folded within the case of device 18. In other embodiments, the antenna may be outside of the device 18 and encased in epoxy resin or other bio-compatible dielectric material. In this way, the usually metal case 24 will not significantly impede RF transmission to and from the antenna of device 18. In addition, also measuring electrodes for impedance and for EKG might be situated within the epoxy header. By way of doing so, the critical feed-through in the otherwise hermetically sealed case might be better protected.

The MICS transceiver 118 enables communication with the implantable medical device 18. It may operate on a different frequency than the GSM bands to avoid interference with radio modem 114. Interface 118 provides high-speed wireless data communication with the implantable device 18, within approximately 6 feet. A stationary base station 100 could be placed near a bed or other location where the patient could be close enough for data transmission. Similarly, a portable device could be worn by the patient.

For data communication with remote locations, such as doctor's offices, base station 100 may include network interface 116. One examples of network interface 116 is an Ethernet Network Interface Card (NIC). Ethernet can be used as an alternative connection to the Internet for uploading patient data, in the event that wireless data service is not available or is prohibitively expensive. Ethernet interface 116 can also be used for remote management and uploading/upgrading system firmware. An optional modem 117 for data transmission using the public switched telephone network may also be incorporated.

An alternative data communication interface for base station 100 is radio modem 114. In certain embodiments, radio modem 114 may be a cellular telephone with a modem, or may operated similarly thereto. Radio modem 114 may couple to an antenna 121 which, in some embodiments, may be external to or remote from the main housing of base station 100. The specific design of the antenna depends on the particular band used, but in any event could conform with GSM 900, 850, 1900, or 1880 standard. Use of a dedicated GSM/GPRS radio modem 114 can reduce system complexity, as this would require only a power supply and a data connection to the system. This reduces overall system complexity.

Data may be transmitted to the Internet using GPRS (General Packet Radio Service) over the GSM band. Alternatively, instead of a self-contained radio modem, a quad-band (or tri-band) GSM/GPRS RF (Radio Frequency) transceiver can be used. However only the radio and associated components are included, so further additional hardware might be required for baseband processing, etc. This can connect to and switch between a greater number of GSM networks, allowing for greater coverage area (and coverage in more countries)

Alternatively, instead of GPRS/GSM, a different cellular data service, such as X.25 or Cellular Digital Packet Data (CDPD) can be used. One preferred embodiment uses a RIM 902M Radio Modem operating in the GSM 900 band. For example, RIM's proprietary Radio Access Protocol could be used to communicate with the modem 114 in this example. Alternatively, if a self-contained radio modem from another manufacturer is used, a different protocol, such as RS-232, may be used.

In yet other embodiments, if a custom GSM/GPRS RF solution is used instead of a self-contained radio modem, a custom interface could be defined, for example using memory-mapped I/O, or simply the GPIO (General Purpose I/O) pins on the controller to communicate with and control the radio.

SIM Card 110 is a Subscriber Identity Module that identifies a particular user of a GSM network. SIM card 110 could be keyed to a Patient ID, for example, for billing purposes. Patient ID could be encrypted and sent separately along with patient data.

It will be appreciated by those skilled in the art that base station 100 may be in data communication with a plurality of implanted devices. For example, base station or repeater 100 could receive pacemaker data from an implanted device of a patient such as the disclosed CHF monitor, a pacemaker, a defibrillator, etc. and store such data and transmit it periodically to a doctor's office. Such a system would permit, for example, daily monitoring of a patient's condition as opposed to occasional visits to a doctor's office.

Depending on the digitization rate, device 18 may generate approximately 16 to 18 megabytes of data per day. Using the system of the present invention, data could be collected by the base station, parsed, analyzed and/or summarized, and periodically sent to a remote facility (such as a doctor's office) on, for example, a quarterly basis. Alternatively, triggering events such as tachycardia or increasing congestion could be used to determine when the base station 100 would open a communications link and send data or alarm signals.

Base station 100 could be used with other implanted sensors which could monitor, for example, blood glucose level, oxygen saturation, temperature or other metabolic parameters. Such monitoring could be useful in tracking the cardiovascular fitness not only of patients, but also soldiers, athletes and others subjected to physical stress or harsh environments such as special mission pilots or astronauts.

Figure 7B:
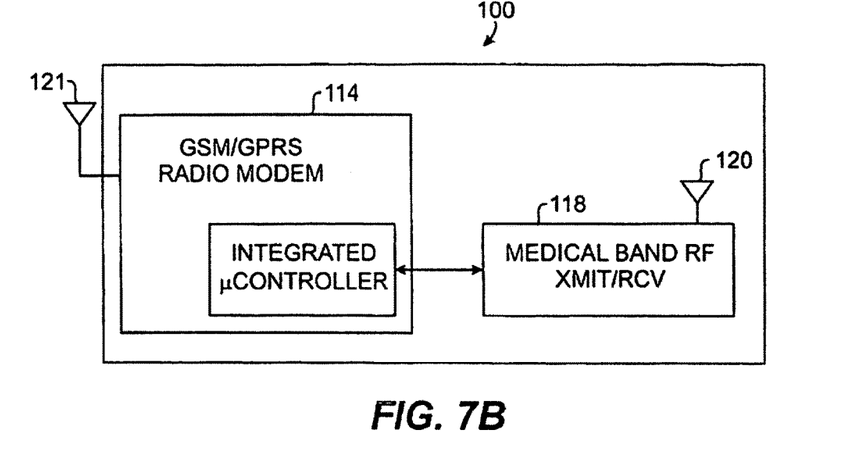
FIG. 7B is a block diagram of an alternative embodiment having a dedicated microcontroller integrating the functions of 210, 211, 212, and 213 in FIG. 8.

FIG. 7B shows an alternative embodiment of the base station having an integrated microcontroller which performs several of the function of the separate function disclosed in FIG. 7A. For clarity, the other system components shown in FIG. 7A have been omitted.

Implantable device 18 could monitor and record the patient's ECG and other physiological parameters. The implantable device has a limited power supply in its on-board battery, and it is desirable to use as little power as possible to maximize the life of the device. For this reason, the implantable device may have internal memory storage capable of buffering or temporarily holding the patient data so it does not need to continuously transmit the patient data. For example, Flash memory or low-power SRAM can be used for memory storage. Flash memory does not consume any power once the data has been stored, however the amount of power consumed during program and erase can be significant. An SRAM requires constant power, but the amount of power is small.

The amount of patient data that is collected per 24-hour period is less than 20 MB. A simple, power-efficient loss-less data compression algorithm may reduce that amount even further, perhaps even in half. A balance between power used to compress the data and power used to transmit the data is desirable.

As mentioned before, for power conservation reasons, the MICS radio need not continuously transmit patient data. The patient data may be collected and stored in the memory storage, and subsequently transferred to the device at predetermined intervals. A portable, wearable device could use an hourly schedule. A stationary device under normal conditions could upload the data on a daily to weekly schedule.

Figure 8:
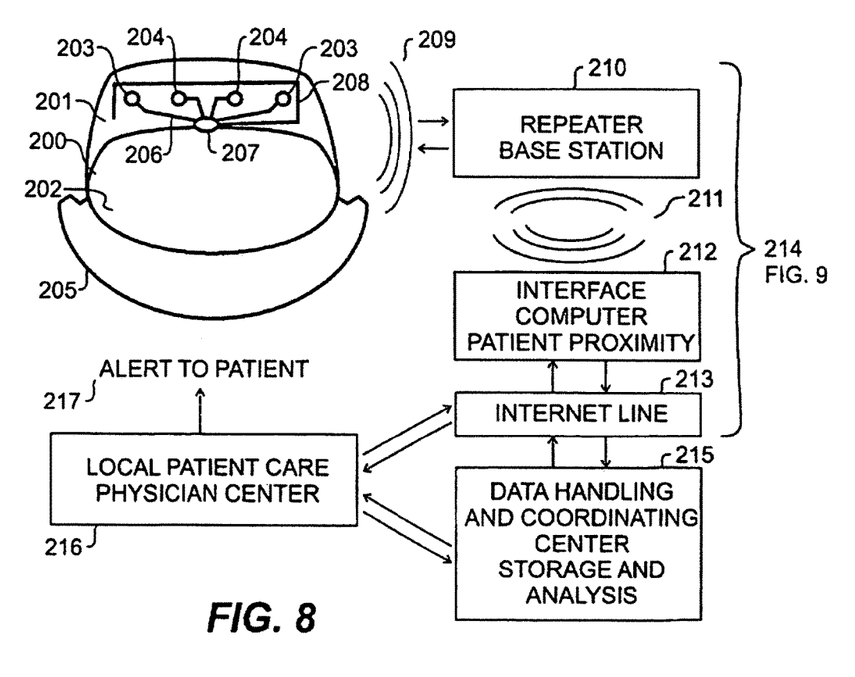
FIG. 8 is a block diagram of system operation through a base/repeater station, a data handling and coordinating center and a local patient care physician center.

FIG. 8 depicts an alternative embodiment of the invention, and specifically shows a device 200 for monitoring CHF implanted in a patient 205. The device 200 has an epoxy header 201 which is on top of medical electronics 202 (e.g., FIG. 3) contained in the hermetically sealed case 200 of the device. The header contains a pair of outer electrodes 203 and a pair of inner electrodes 204. Those electrodes are connected through wires 206 which communicate with medical electronic 202 through the feedthrough 207. In addition, an antenna 208 is incorporated in the epoxy header for communicating signals in the medical implant communications service bands. An antenna 208 having a length of ¼ lambda may be used to transmit signals effectively. Through radio frequency radiation 209, the device communicates with the base station or repeater 210 (similar to base station 100 of FIG. 7A for example) in the proximity of the implant patient 205. The base station 210, which receives the signals from the implant device 200, can transfer and/or amplify the signals, which in turn can be easily communicated through a wireless local network or a personal area network 211 to the interface of a computer 212, preferably also in the proximity of the patient. Further connections through Internet lines 213 occur with a data handing and coordinating center 215 for further storage and analysis of this data. Instead of a repeater 210, communication pathway 211 and communication computer 212, a single unit 214 as shown in FIGS. 7A and 7B is feasible.

The data handling and coordination center 215 primarily receives the data either in a continuous manner, in a temporary intermittent manner, or in a predetermined activated manner as dictated by the implant device 200. Signals can be received either as live or stored data, or as preprocessed data, or as data that fulfill certain selection criteria (such as an alarm condition). The data transfer occurs intermittently or continuously. The transfer of the stored data for one day, for example, can occur at certain fixed time periods (e.g., at night) or when the patient is in the proximity of the local repeater. This proximity is defined dependent on the power output of the device through the medical implant service bandwidth and preferably is kept at a low level to conserve battery life, battery power, and to extend the life of the implant device.

Also, to preserve energy and optimize the capacity of all links involved in the data processing, data is preferably only sent if they fulfill certain criteria. The criteria can be incorporated in the logic or programming of the circuitry 202 of the implant device 200 or within similar logic or program of the base station 210. Despite such criteria, data indicative of an emergency condition can be made to transfer on a priority basis, such as immediately, if sensor data from the device 200 indicates a life threatening condition such as tachycardia or an abnormal slow rate, which in turn could prompt immediate intervention by a physician and/or transfer of the patient to an emergency room. The emergency condition can be accompanied by an alert 217, which can be communicated to both the patient (via links 213, 212, 211, 210, and 209), and to a local patient care physician center 216. The alert may be manifested to the patient from a audible sound, vibration, or some other physical indicator emanating from the device 200. Either way, a physician at the center 216 and/or the patient can then establish communication with each other through traditional means (Internet, phone, e-mail, direct physical presence, etc.). As communication with the device is two-way, the doctor may also request additional data from the device, and/or can program the device 200 to perhaps better assist the health of the patient.

Because electrodes 203 and 204 are situated outside the hermetically sealed case in a nonmetallic header 201, preferably a polymer of epoxy resin, the feedthrough 207, which is the most sensitive point in the hostile environment of the human body, can be protected. Moreover, as well as providing mechanical shielding for the feedthrough 207, the header 201 provides electrical shielding. Moreover, the header 201 preferably contains the MICS-band antenna 208, which will suffer less attenuation than were the antenna disposed within the hermetically sealed metallic case 200 of the device. As shown, the same electronic feedthrough 207 is used for both the antenna 208 and the electrodes 203, 204, but different feedthroughs may also be used.

For data storage, the device electronics 202 can digitize the data accordingly to its signal characteristics. For example, the EKG can be digitized with a sampling frequency of 100 Hz. If this is done, the resulting quantity for one day would roughly constitute 8 to 9 megabytes. An activity signal of a miniaturized accelerometer which is also incorporated in the hermetically sealed device and preferably situated on hybrid electronic circuitry 202 can be digitized at a much slower rate in a range of 10 Hz, perhaps amounting to less than 1 megabytes of data per day. For the impedance measurements, as described in the referenced and related applications, another 8 megabytes could be required bringing the daily data amount to roughly 16 to 20 megabytes. Modern storage memories incorporatable into the device 200 can easily handle such data, and a memory of 256 mega bits could handle the data for nearly 2 weeks. In short, data for a whole host of patient parameters can be stored and periodically transferred, say every other day or week, unless built-in data handling and analysis triggers an earlier transmission of the data (such as during an emergency condition).

Figure 9:
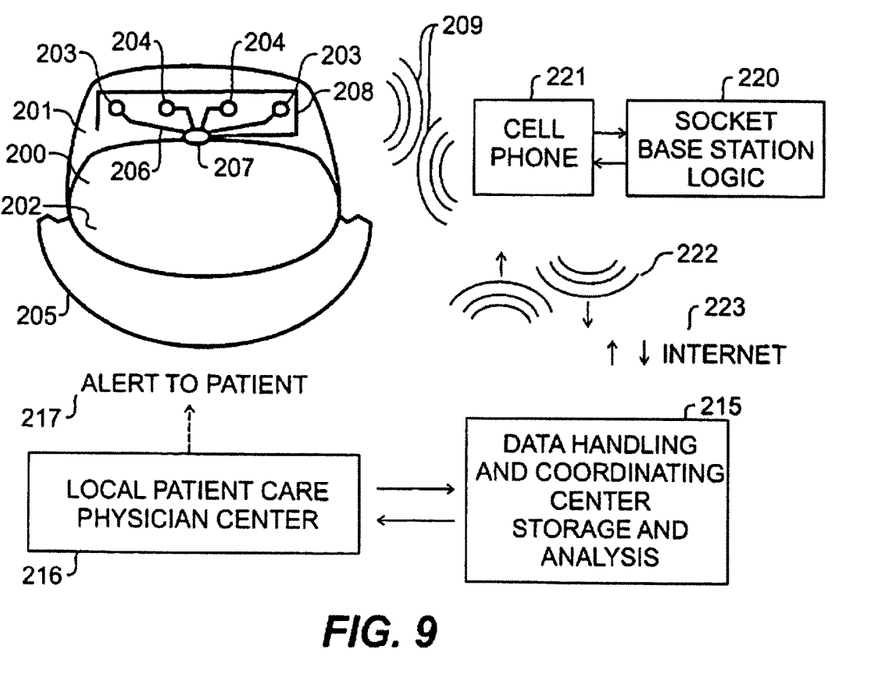
FIG. 9 is a block diagram of another exemplary embodiment of the invention.

FIG. 9 illustrates another embodiment of the present invention. In this case, the implant device 200 is comparable to the device described in FIG. 8. However, in this embodiment, communication occurs with a cell phone 221 which acts as a repeater/base station programmed with appropriate logic 220 to perform the function of the base station as discussed above. Such logic 220 can appear within the phone 221 itself, or in a traditional phone socket or cradle. Cell phone 221 communicates via an RF interface with the implant device 200, and further communicates via an RF telephone link 222 to, for example, the Internet 223, which can comprise one network intervening between the phone 221 and the coordination center 215, where data is stored and/or analyzed. (one skilled in the art will realize that other communication networks in addition to the Internet would logically be used, but are not shown). Alerts indicative of emergency conditions can be sent to the patient via the Internet 223 either to the cell phone, or through wireless cell phone communication from the patient care center 216 to cell phone 221. Further communication of the alert to the patient can then be communicated through radio frequency link 209 to the device 200. On the other hand, the local patent care physician center 216 can alert the patient through communication link 217, which may be direct access, email, phone calls or physical presence of a person to assist the patient and resolve the current medical situation.

Figure 10:
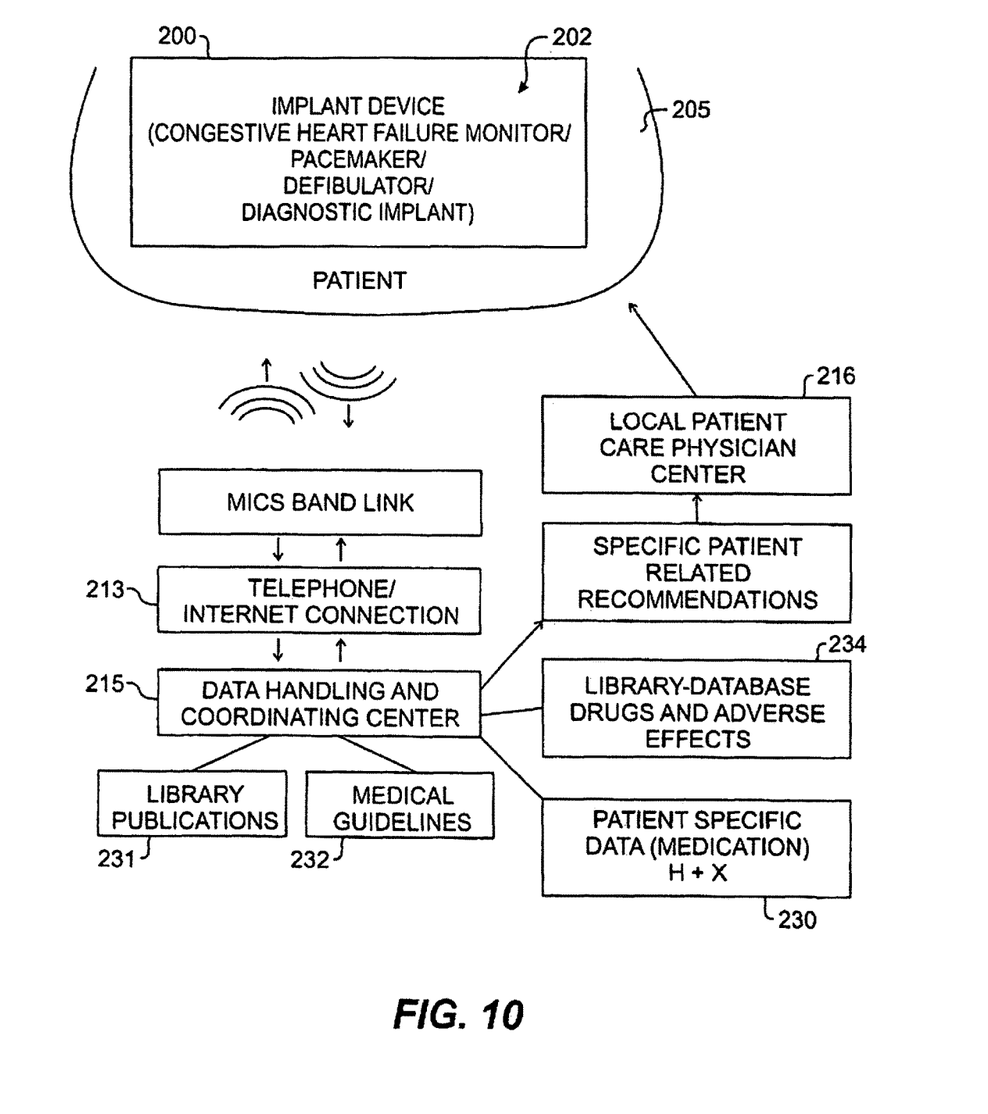
FIG. 10 illustrates the advanced processing and analysis of information derived from patients' history, physical examination, current medication, patient related parameters and the actual and/or previous data received from a patient implant device such as a heart failure monitor, ECG monitor, activity sensor, pacemaker, defibrillator or other diagnostic or therapeutic electronic implant in the patient's body. The data from the implant device may be analyzed, evaluated and/or commented in light of evidence-based medicine by using input from the library with medical publications, drug action and adverse effects, medical guidelines in order to provide a specific patient tailored recommendation.

FIG. 10 illustrates an advanced method of information technology and handling. The implant device 200 communicates through the mobile implant communication service band through links as described previously either through wireless, telephone, Internet, or land line telephone with the data handling and coordinating center 215. In this center 215, evaluation of the data from the device 200 may be accomplished as before, but, in addition, other patient specific data like patient history, current medication, age, and other patient relevant information is assessed, as pulled from database 230. Furthermore, analysis can be further assisted via data pulled from a library database 231 of current articles, from a medicine guidelines database containing recommendations for certain patient conditions, and from a drugs and adverse effect database 234. This culmination of data (current patient data from device 200, historical patient data, etc.), can be used at center 215 to provide, in automated or semi-automated fashion, the best course of action or recommendation for a particular patient. This recommendation can be transmitted to the local patient care physician center 216 to allow a better evaluation of what might be done with the patient and what kind of measures could be given. It is up to the physician to communicate this kind of decision and recommendation to the patient including any action such as taking diuretics, new medications, beta blockers, antiarrhythmias, or the recommendation for implant of a brady- or tachyarrhythmia device.

Implanted devices 200 may be programmed via the base station 210 and its associated data link(s). Such programming could replace the magnetic wand programming of the prior art which typically must be performed in a healthcare facility or doctor's office.

By using the system of the present invention, implanted devices may be reduced in physical size. Implanted devices used in conjunction with the base station provide the benefit for allowing store and intermittent transfer of data. Sending data in short bursts not only conserves power (permitting smaller batteries to be used in the devices 200), but also reduces the potential time window for interference and provides more forgiving power supply requirements. This is important for implant systems, which frequently use batteries with high impedance. This approach also makes the use of a very high data transmission rate attractive for intermittent telemetry applications, such as in pacemakers, as a large capacitor can have its charge mortgaged for the period of the radio transmission, and then recharged at a lower rate. Another fact that points in favor of a high data rate is that the transmission will occur during a shorter time period, making it possible for more users to share the same radio channel.

Although a presently contemplated best mode, preferred embodiment and method of practicing the invention have been described in this specification, it will be apparent to those skilled in the art from a consideration of the foregoing description that variations and modifications of the disclosed embodiments and methods may be made without departing from the spirit and scope of the invention. It is therefore intended that the invention shall be limited only to the extent required by the appended claims and the rules and principles of applicable law.

The invention claimed is:

1. A device-implemented method of detecting and monitoring an event indicative of congestive heart failure in a patient, comprising:
    implanting the device on a lower left anterior lateral hemithorax of the patient;
    performing ongoing measurements of impedance of a portion of the patient's body generally occupied by the lungs, said measurements of impedance being indicative, at least in part, of said event indicative of congestive heart failure;
    transmitting transmissions including said measurements of impedance to a base station at a transmission time being based, at least in part, on an occurrence of the event indicative of congestive heart failure using a radio transmitter; and
    sending data relating to said measurements of impedance from the base station to a remote location via a telecommunications network.

* * * * *